United States Patent [19]

Keyes

[11] Patent Number: 4,713,335

[45] Date of Patent: * Dec. 15, 1987

[54] PROTEIN MODIFICATION TO PROVIDE ENZYME ACTIVITY

[75] Inventor: Melvin H. Keyes, Sylvania, Ohio

[73] Assignee: Owens-Illinois Glass Container Inc., Toledo, Ohio

[*] Notice: The portion of the term of this patent subsequent to Sep. 2, 2003 has been disclaimed.

[21] Appl. No.: 476,954

[22] Filed: Mar. 21, 1983

Related U.S. Application Data

[63] Continuation of Ser. No. 418,344, Sep. 15, 1982, abandoned.

[51] Int. Cl.$^4$ .......................... C12N 9/00; C12N 9/14
[52] U.S. Cl. .................................... 435/183; 435/195; 530/402
[58] Field of Search ............... 435/183, 184, 188, 199, 435/200, 201, 203, 195, 350; 260/112, 121; 530/262

[56] References Cited

U.S. PATENT DOCUMENTS 4,609,925  9/1986  Keyes et al. .................. 435/188 X

OTHER PUBLICATIONS

Battelle Report, Verification of Semisynthetic Activity, Owens-Illinois, Jul. 14, 1981.
Yamauchi, et al., Reversible Conversion of Lysine Monooxygenase to an Oxidase, *J. of Biol Chem.*, vol. 248, 1973, pp. 3750–3752.
Mahler et al., *Biological Chemistry*, 1966, Harper and Row, N.Y., pp. 287–295.
Beaven et al., *International Journal of Peptide Research*, vol. 5, pp. 215–218, 1973.

Primary Examiner—David M. Naff
Attorney, Agent, or Firm—H. G. Bruss

[57] ABSTRACT

A naturally occurring protein is chemically modified to provide the protein with activity of a selected enzyme. The protein does not contain activity of the selected enzyme before modification. Modification is carried out by grossly denaturing the protein, partially renaturing the protein to form a partially denatured protein, contacting the partially denatured protein with an enzyme inhibitor of the selected enzyme, crosslinking the protein in the presence of the inhibitor and recovering a modified protein having activity of the selected enzyme.

28 Claims, No Drawings

PROTEIN MODIFICATION TO PROVIDE ENZYME ACTIVITY

This is a continuation of application Ser. No. 418,344 filed Sept. 15, 1982, now abandoned.

BACKGROUND OF THE INVENTION

1. Field Of The Invention

Proteins are biologically synthesized macromolecules having various role in living systems. Enzymes are particular varieties of biologically-active proteins which catalyze specific reactions. Presently, enzyme technology is used in many areas in industry and research such as, for example, medical research, food processing and preservation, the production of fermented beverages, the production of pharmaceuticals and the analytical determination of the concentration of various metabolites and food components by analytical enzyme techniques.

Enzymes are highly specific in their biological activity and generally catalyze a particular reaction at a very high rate compared to the corresponding reaction occurring at room temperature without biological catalysis. One enzyme may show catalytic activity with respect to a number of substrates upon which it can act. Accordingly, a given enzyme may catalyze the synthesis or degradation of more than one substrate. Some proteins which are not considered classical enzymes, such as bovine serum albumin, show very limited catalytic activity with respect to one or more substrates.

Many enzymes are found in nature in very small quantities. Accordingly, their isolation, purification and use is limited to a small scale operation in view of the expense and time needed to isolate them in a useful form.

Some enzymes occur in nature in relatively large quantities and are relatively easy to isolate, purify and use. Unfortunately, due to the precise catalytic behavior of the enzymes, the enzymes available in large quantities can only catalyze certain select reactions.

Much effort has been directed recently toward the synthesis of synthetic biological catalysts which exhibit enzymatic behavior similar to the enzymatic behavior exhibited by native enzymes which are either scarce or expensive to isolate. Further, some attempts have been made to modify native enzymes to change their enzymatic specificity so that they may function to catalyze a reaction which they previously could not catalyze.

2. Description Of The References

One technique known to achieve enzyme behavior to catalyze a specific desired reaction is the synthesis of so-called enzyme model molecules. For example, low molecular weight compounds may be covalently bonded to functional groups which exhibit the activity of the active site of an enzyme. Examples of such preparations are described in the publications: Breslow, R., *Advances in Chemistry Series,* R. F. Grould, Ed., American Chemical Society, Washington, D. C. 21–43 (1971) and Tang, C. C.; Davalian, D.; Haung, P. and Breslow, R., *J. Amer. Chem. Soc.,* 100, 3918 (1978) and Breslow, R., Doherty, J., Guillot, G. and Lipsey, C., *J. Amer. Chem. Soc.,* 100, 3227 (1978).

Another technique involves the use of a synthetic polymer matrix which is modified along its backbone to provide functional groups which exhibit the function of the active site of a given enzyme. Examples of such techniques can be found in the following articles: Wulff, G. and Schulza, I., *Israel J. Chem.,* 17, 291 (1978) and Suh, J. and Klotz, I. M., *Bioorganic Chemistry,* 6, 165 (1977).

Another technique involves the attachment of a new chemical moiety to a native enzyme near the active site of the enzyme to attempt to cause such enzyme to react with a different catalytic activity. One example of this is the conversion of papain, a proteolytic enzyme to an oxidase type enzyme by the covalent attachment of a flavin near the active site of the native papain enzyme, as illustrated in the articles: Levine, H. L. and Kaiser, E. T., *J. Amer. Chem. Soc.,* 100, 7670 (1978), Kaiser, E. T., et al, *Adv. In Chemistry Series,* No. 191, Biomimetic Chemistry, page 35, 1980; and Otsuki, T.; Nakagawa, Y. and Kaiser, E. T., *J.C.S. Chem. Comm.,* 11,457 (1978). Other examples of such enzymatic modification may be found in the article: Wilson, M. E. and Whitesides, G. M., *J. Amer. Chem. Soc.,* 100, 306 (1978).

Still another attempt to change enzyme specificity is the immobilization of a native enzyme into a gel matrix. For example, trypsin enzyme has been immobilized in polyacrylamide gel. The polyacrylamide gel allows amino acid esters to diffuse through the gel matrix to react with the enzyme but will not allow larger proteins to diffuse through. Thus, the enzyme specificity is changed by eliminating access of one of the substrate molecules to the enzyme.

The immobilization of native enzymes is well established in the art. Also, examples of enzyme specificity changes by immobilization are known in the art. Both immobilization and enzyme specificity changes are described in the *Kirk-Othmer Encyclopedia of Chemical Technology,* 3 Ed., 9, 148 (1980) published by Wiley and Son, Inc.

Two other methods relating to enzyme immobilization are disclosed in U.S. Pat. Nos. 3,802,997 and 3,930,950. In U.S. Pat. No.3,802,997, a method of stabilizing enzymes by bonding the enzymes to inorganic carriers, in the presence of their substrates, whereby the enzyme is immobilized, is disclosed. In U.S. Pat. No. 3,930,950, a method of enzyme immobilization is disclosed wherein an active support member is provided which is capable of reacting with an enzyme to become chemically bonded thereto. Subsequently, the active support is contacted with an enzyme-substrate complex which has been formed by mixing together an enzyme and a specific substrate, while minimizing the transformation of substrate to product. Thus, the enzyme component of the complex becomes chemically bonded to the support member.

Also, it has been known that a native lysine mono-oxygenase can be reacted to block the sulfhydryl groups on the enzyme. When the specific enzyme lysine mono-oxygenase is so treated, it shows new catalytic activity toward amino acids and catalyses oxidative deamination instead of its natural oxygenative decarboxylation. However, the reporters cannot account for the modified behavior. See the article by Yamauchi, T.; Yamamoto, S. and Hayaishi, O., in *The Journal of Biological Chemistry,* 248, 10, 3750–3752 (1973). Also, it has been reported that by reacting a native enzyme, for example trypsin, with its natural inhibitor, and subsequently cross-linking the enzyme, its activity with respect to its natural substrates can be modified. See the article by Beaven, G. H. and Gratzer, W. B. in *Int. J. Peptide Res.,* 5, 215–18 (1973).

Also, synthetic proteins have been synthesized by the anchoring of an amino acid residue on a solid support and subsequently adding amino acid residues one after another.

Further, semisynthetic proteins have been synthesized by a method wherein a native protein is subjected to limited hydrolysis to produce protein fragments. The fragments of the native protein are then subjected to a process whereby one or more amino acid residues are added or removed from the fragments to form modified fragments. The resultant modified fragments are then reattached to form the semisynthetic protein with an altered amino acid residue composition. Examples of the synthetic and semisynthetic protein technologies cited immediately above are found in the book *Semisynthetic Proteins* by R. E. Offord, published by John Wiley and Sons Ltd., copyrighted in 1980.

While these techniques are suitable for many applications, a need exists for a simple, efficient, economical and systematic method for chemically modifying an inexpensive and commercially available native protein to produce an enzyme-like modified protein. The protein can show a catalytic enzymatic activity with respect to a desired chemical reaction which was not previously a commercially-useful reaction catalyzed by the native enzyme and which new reaction can be predetermined in a systematic fashion. The methods disclosed in the above-disclosed references simply subject an enzyme to a set of conditions and attempt to eludicate its behavior. They fail to provide a systematic method to modify protein characteristics.

SUMMARY OF THE INVENTION

The present invention achieves an enzyme-like modified protein by converting a naturally occurring so-called native protein to an enzyme-like modified protein exhibiting different characteristics than the native protein starting material.

In one embodiment of the invention, a native protein is grossly denatured by contacting the native protein with a denaturing agent, for a time and at a concentration sufficient to cause essentially gross protein denaturation. Next, the grossly denatured protein is subjected to conditions that cause the partial renaturation of the protein to produce a partially denatured native protein. The partially denatured protein is contacted with an inhibitor of a model enzyme, whose catalytic activity is to be modeled, to form a partially denatured protein-inhibitor complex. The partially denatured protein in the complex is next cross-linked to produce a new enzyme-like modified protein.

Subsequently, the model enzyme inhibitor and any excess cross-linking agent are removed from the newly formed enzyme-like modified protein to yield a functional, stable, analogue to the model enzyme. The enzyme-like modified protein thusly produced exhibits the catalytic activity characteristics of the model enzyme

DETAILED DESCRIPTION OF THE INVENTION

In attaining the advantages of the present invention, it has been discovered that a protein can be modified from its native conformation to a modified conformation by practicing the process of the present invention. The new conformational state defines an enzyme-like modified protein.

As used herein, the word "enzyme" is defined as a protein which has well-known catalytic activity toward specific substrates. The term "protein" as used herein is defined as generally accepted in the art, to wit, a polypeptide formed of amino acids to yield a biological molecule.

The process of the present invention comprises chemically modifying a native protein from one conformation, its natural or native state, to a second conformation, a new modified state. The process produces a new, enzyme-like modified protein which is produced to yield a stable, new enzyme-like modified protein which models one or more of the enzymatic activity characteristics of the selected model enzyme.

In the preferred embodiment of the invention, a native protein is selected which is to be chemically modified to produce the new enzyme-like modified protein analogue of a desired model enzyme. The process of the present invention converts the soluble native protein, which does not possess the desired catalytic activity, namely the enzymatic catalysis behavior of the model enzyme, into a stable, enzyme-like modified protein which mimics or copies the biological catalytic activity characteristics of the model enzyme.

A preferred way of carrying out the novel process of the present invention for chemically modifying a native protein to produce a predetermined enzyme-like modified protein comprises the steps of: grossly denaturing the native protein by contacting the native protein with a denaturing agent, for a time and at a concentration sufficient to grossly denature the native protein; partially renaturing the grossly denatured protein to produce an only partially denatured protein by contacting the grossly denatured protein with reagents or process conditions sufficient to partially renature or refold the protein; contacting the resultant only partially denatured protein with an inhibitor for a selected model enzyme, for a time sufficient and a temperature sufficient, to produce a partially denatured protein-inhibitor complex and subsequently cross-linking the partially denatured protein in the complex to form the new, stable enzyme-like modified protein by contacting the partially denatured protein with a cross-linking agent. Any excess cross linking agent and the model enzyme inhibitor are removed from the newly created enzyme-like modified protein to isolate the new, catalytically active enzyme-like modified protein product.

While in the preferred embodiment, a nonenzymatic native protein starting materials or so-called host protein is converted into a catalytically active, enzyme-like modified protein, the conversion of any native protein to an enzyme-like modified protein analogue of a model enzyme is contemplated herein. Generally, native or host proteins which are most readily available for conversion into an enzyme-like modified form are nonenzymatic proteins, like bovine serum albumin. Preferably, the native protein starting material is selected because it is available in reasonably pure form, in commercially useful quantities, at reasonable unit costs. However, as exemplified hereinafter, any protein can be used as the native protein starting material, either enzymatic or nonenzymatic proteins. Typically nonenzymatic proteins, like bovine serum albumin, are available in pure form, in large quantities at lower cost than enzymatic proteins, and are thus preferred starting materials.

As disclosed above, the starting material native protein is grossly denatured or unfolded to essentially destroy its native three dimensional chemical structure. Next, to achieve a protein structure which is capable of binding inhibitor, although not the native structure, the grossly denatured protein is partially refolded to produce a partially denatured protein. The partially denatured protein has neither the chemical structure, so-called conformation, of its parent, the native protein starting material, or of the grossly denatured protein it was produced immediately from. While not being bound by any theory, it is believed that the gross denaturation of the native protein starting material and then only partial refolding thereof allow for potential new inhibitor binding sites to be generated. Thus, different sites are generated than would be available if the native protein itself were partially denatured without going through a gross denaturation step prior to contacting the protein with the inhibitor.

As used herein, the phrase "grossly denatured" is defined as generally accepted in the art, to wit, a major change from the native state which causes the protein to become essentially completely unfolded. In the grossly denatured state, the protein lacks both secondary and tertiary structure and resembles a random coil. The grossly denatured state can be determined by comparison of physical measurements of the grossly denatured protein to those of a model random coil. Examples of such physical measurements for the determination of gross denaturation are viscosity, circular dichroism, sedimentation coefficient and ultraviolet spectra. Within the definition of grossly denatured proteins are some protein which may contain a trace of residual secondary and/or tertiary structure. Such traces of residual structure do not adversely effect the operation of the present invention.

The characteristics of grossly denatured proteins are well-known in the art. For example, when using a viscosity measurement to monitor protein denaturation, the viscosity of a globular protein generally goes up during the unfolding process. On the other hand, the viscosity of fibrous protein is quite large in the native state and may either increase or decrease upon unfolding. Such measurement changes during denaturation are well listed in the literature as described hereinafter. Unfolding can also be monitored by the change in ultraviolet spectra. The major change in spectra occurs because of the transfer of phenylalanyl, trypyl, and tryptophyl side chains from the protein interior to the solvent environment during denaturation. Generally the molar absorptivity will decrease at some wavelengths while increasing at others due to the shift in absorption bands. The gross denaturation of protein structure dramatically changes the optical rotation and circular dichroism spectra. The exact nature of the changes relate to the secondary and tertiary structure of the native protein. These physical parameters, used to determine gross denaturation, as well as many others, can be monitored to determine when a protein is grossly denatured as described in many papers on protein denaturation such as: Charles Tanford, *Advances in Protein Chemistry*, 23, 121 (1968).

Several review articles describe the process of gross denaturation and the criteria for demonstrating gross denaturation in terms generally accepted in the art and used according to this invention, namely, the following articles, Charles Tanford, *Adv. Protein Chemistry*, 23, 121 (1968); P. L. Privalov, *Adv. Protein Chemistry*, 33, 167 (1979); and C. B. Anfinsen, *Science*, 181, 223 (1973).

The preferred methods of protein gross denaturation according to the invention are as follows.

Gross denaturation of a native protein starting material can be achieved for most proteins by the use of guanidine hydrochloride (GuHCl). Gross protein denaturation is usually complete by concentrations of from 6 to 8 M GuHCl. In many instances, urea can be substituted for GuHCl in a concentration of about 8 M to achieve gross denaturation. Gross denaturation can also be achieved by raising the temperature until the well recognized unfolding transition takes place. Moreover extremes of acidic or basic conditions alone or in combination with temperature can be used. Generally, for most proteins a temperature on the order of 50°–70° C. is sufficient to grossly denature the native protein starting material. Suitable acids for gross denaturation include acetic, formic, propionic and citric, while suitable bases include sodium and potassium hydroxide. Suitable inorganic acids as denaturing agents include nitric, phosphoric, sulfuric and hydrochloric.

When the gross denaturing conditions are reduced the protein molecules becomes partially renatured. This partially renatured state may consist of protein molecules that remain nearly totally denatured mixed with other molecules are nearly completely refolded. In the alternative, nearly all protein molecules are nearly completely refolded. In the alternative, nearly all protein molecules could be partially and nearly equally refolded. The exact physical state of the partially renatured protein is not critical to the present invention. The partially renatured protein state will be recognized by the changes in physical parameters which indicate that the protein is no longer a random coil but contains considerable secondary and tertiary structure. The partially renatured state, however, lacks the highly ordered structure of the native protein state and is believed to afford different potential sites for inhibitor binding than a partially denatured native protein. The partially renatured protein is believed to offer different binding sites for the inhibitor since it has been completely structurally rearranged due to the gross denaturation step. The grossly denatured protein can be partially renatured to offer new sites, not previously offered in a partially denatured native protein, for inhibitor binding.

The partial renaturation of grossly denatured proteins is well known in the art and discussed in detail in the following references:

L. G. Chavez, Jr. and H. A. Scheraga, *Biochemistry*, (1980), 19, 996–1004; H. Taniuchi and C. B. Anfinsin (1968), *J. Biol. Chem.*, 243, 4778; H. Taniuchi and C. B. Anfinsin (1969), *J. Biol. Chem.*, 244, 3864; M. I. Kanehisa and T. Y. Tsong, *Biopolymers*, 18, 2913–2928 (1979); E. W. Miles, K. Yutani, and K. Ogasachara, *Biochemistry*, 21, 11, (1982) and D. B. Witlanfer, *Adv. Protein Chemistry*, 34, 61 (1981).

After the protein is partially renatured it is contacted with an inhibitor of a model enzyme whose catalytic activity is to be mimicked.

As used herein, the term "inhibitor" means any compound with sufficient structural similarity to the natural substrate of a model enzyme to serve as a template for the catalytic site of the enzyme-like modified protein. In the preferred embodiment of the preparation of an enzyme-like modified protein, the inhibitor is any of the known classical inhibitors for a given model enzyme. However, as used herein "inhibitor" can include any molecule with sufficient structural similarity to the classical inhibitor to preserve an inhibitor like site on the modified protein. The natural substrate of the model enzyme can act as the inhibitor or template for the modified protein in many cases. Inhibitors are generally not degraded by the enzyme, as are substrates, and serve to more readily preserve a catalytic site than the natural substrate. One example of the structural similarity of an enzyme inhibitor and the natural substrate of an enzyme is the case of glucose oxidase. Glucose is the natural substrate of glucose oxidase while D-glucal is the inhibitor for glucose oxidase. Glucose and D-glucal are very structurally similar.

In the preferred embodiment, after the partially renatured protein has been contacted with the inhibitor for a time sufficient and at a temperature sufficient to form the protein-inhibitor complex the partially renatured protein portion of the complex is cross-linked to stabilize the new structure.

As used herein, the term "cross-linking" means the formation of covalent bonds between reactive sites on a protein. Generally, protein cross-linking is accomplished by the use of multifunctional reagents such as glutaraldehyde. Other examples of suitable cross-linking reagents to effect the cross-linking of a protein are: 2-amino-4, 6-dichloro-s-triazine; diazonium salts; N-hydroxysuccinamide; p-benzoylazide and those reagents disclosed in the following references: Wold, F., *Methods Enzymol*, 11, edited by C. H. W. Hirs, C.H.W., Academic Press, 967, 617; Fasold, H. et al., *Augen. Chem. Int. Ed. Engl.*, 10, 795, 197 and Keyes, M. H., in the *Kirk-Othmer Encyclopedia of Chemical Technology*, 9, 3rd Ed., 1980, J. Wiley & Sons, Inc., 148–172. Cross-linking may also be achieved by disulphide rearrangement.

One preferred process to grossly denature a native protein starting material with beta-mercaptoethanol is the following. The native protein is admixed with beta-mercaptoethanol in a molar ratio of about 1000 units of beta-mercaptoethanol to one unit of protein. After treatment with beta-mercaptoethanol, at neutral pH, for one to several hours, quanidine hydrochloric is added to a concentration of 6 M. These conditions are sufficient to totally denature most proteins. Preferably, the concentration of protein and pH should be such that part or most of the protein remains in solution. The beta-mercaptoethanol cleaves disulphide bridges and facilitates the gross denaturation of the protein by assisting in structure degradation.

In the preferred embodiment of the invention, a native protein or host protein showing little or no catalytic activity with respect to a selected substrate is converted chemically by the process of the present invention into an enzyme-like modified protein analogue of a model enzyme. Many enzymes are susceptible to modeling or mimicking by the present process to produce their enzyme-like modified protein analogues from selected native protein starting materials. Examples of such model enzymes which are subject to enzyme-like modified protein analogue production are hydrolytic enzymes, redox enzymes and transferase enzymes. By way of example: The first group, hydrolytic enzymes include proteolytic enzymes which hydrolyze proteins, e.g., papain, ficin, pepsin, trypsin, chymotrypsin, bromelin, keratinase; carbohydrases which hydrolyze carbohydrates, e.g., cellulase, amylase, maltase, pectinase, chitanase; esterases which hydrolyze esters, e.g., lipase, cholinesterase, lecithinase, alkaline and acid phosphateases; nucleases which hydrolyze nucleic acid, e.g., ribonuclease, deoxyribonuclease; and amidases which hydrolyze amines, e.g., arginase, asparaginase, glutinase, histidase, and urease. The second group are redox enzymes that catalyze oxidation or reduction reactions. These include glucose oxidase, xanthine oxidase, catalase, peroxidase, lipoxidase, and cytochrome reductase. In the third group are transferase enzymes that transfer groups from one molecule to another. Examples of these are glutamicpyruvic transaminase, glutamicoxalacetic transaminase, transmethylase, phosphopyruvic transphosphorylase.

In the usual practice of the present invention, one selects a first or model enzyme. One then selects a second native or so-called host protein to be modeled after the model enzyme to produce an enzyme-like modified protein. As discussed above, in many cases the native protein is itself enzymatically active, with respect to a given substrate, since many common enzymes are available in large quantities at fairly low costs in homogeneous sample form. However, nonenzymatic proteins are equally useful when they can be either purchased in pure form or purified by conventional means for use with the present process. One example of such a nonenzymatic protein which may be used as a native protein for the starting material of the bovine serum albumin (BSA). BSA is available in relatively pure form at fairly low cost from numerous commercial sources.

By practicing the process of the present invention, one can custom-tailor the native protein to a different stable enzyme-like modified protein form which shows the catalytic activity characteristics of the enzyme which has been modeled. The ability to custom-tailor a native protein into a predetermined catalytic activity provides greater advantages in a wide range of chemical and industrial situations. For example, if one wishes to use an enzyme which is in short supply, is very expensive or very difficult to isolate and/or purify, such an enzyme may serve as a model enzyme for the preparation of an enzyme-like modified protein analogue by the present process to mimic its activity.

Thus, a native protein which is available in large quantities or at low cost can-be reformed or modified by the process of the present invention to convert the available native protein starting material into an enzyme-like modified protein form of a less available and/or more expensive enzyme.

In the preferred embodiment of the invention, a native protein starting material is purified and dissolved in a near neutral aqueous solvent in the presence of a suitable buffer to maintain the solution near neutrality. Subsequently, the native protein is grossly denatured by any of the expedients described hereinabove to produce a grossly denatured, preferably, soluble form of the native protein starting material. Next, the grossly denatured protein is partially renatured or refolded to produce a partially denatured protein. Subsequently, an inhibitor for the model enzyme is admixed with the partially denatured protein. Sufficient time and sufficient temperature are provided for a partially denatured protein-inhibitor complex to form. Subsequently, to preserve the new, enzyme-like modified protein, the partially denatured native protein portion of the protein-inhibitor complex must be stabilized.

The new protein is stabilized by cross-linking of the protein to produce the enzyme-like modified protein. Often, cross-linking is done as disclosed above by glutaraldehyde cross-linking agent since it is inexpensive. However, any of the above-described cross-linking agents can be utilized effectively in the conventional manner.

The process of the present invention produces a new, enzyme-like modified protein which exhibits a number of advantages and uses. By the discoveries of the present invention an enzyme-like modified protein can be produced which is stable and exhibits a new enzyme-like catalytic activity which was not present in the native protein. Such modified proteins showing enzyme-like catalytic behavior are useful to perform catalytic anabolic and catabolic reactions instead of a naturally occurring enzyme.

In all embodiments of the present invention the inhibitor of the model enzyme is removed after synthesis of the enzyme-like modified protein. Typically repeated washings of the immobilized modified protein is sufficient to remove the inhibitor. Buffered aqueous solution can also be used to remove the inhibitor, such buffers are exemplified hereinafter.

For convenience of disclosure, all patent documents and publications mentioned herein above are incorporated by reference.

Other embodiments of the present invention will be apparent to those of ordinary skill in the art from a consideration of this specification or practice of invention disclosed herein. It is intended that the Examples in the specification be considered as exemplary only with the scope and spirit of the invention being indicated by the claims. The following Examples are exemplary of the various embodiments of the process of the present invention discussed hereinabove.

EXAMPLE 1

Sixty mg of chromatographically purified pancreatic ribonuclease (RNase) native enzyme, purchased from Sigma Chemical Company, lot 110F-02051, type IIA, No. R-5000, is dissolved in 3 ml of 8 M urea denaturing agent containing 0.1 M 2-amino-2-(hydroxymethyl)-1,3-propanediol-HCl buffer (hereinafter tris buffer), at pH 8 with slow stirring at 25° C.

Next, 0.1 ml of neat beta-mercaptoethanol denaturing agent is added in the solution to break disulphide bonds. The resulting solution is shaken slowly for 15 minutes at 25° C. The solution is then placed in a stoppered erlenmeyer flash under a nitrogen atmosphere for 16 hours at 25° C. The closed environment of the flask is maintained by a pressurized nitrogen tank releasing nitrogen gas into the flask with the flask vented into a water trap.

Next, 3 ml of the solution is chromatographed across a gel filtration column, which is 12 in. × 1 in., containing Sephadex brand G-15 gel filtration material. Sephadex is a cross-linked, beaded, high molecular weight polysaccharide which has been cross-linked with epichlorohydrin, marketed by Pharmacia Fine Chemicals. Acetic acid at 0.1 M pH 3, is used as the eluant for the gel column. The eluant flow rate is maintained at 1 ml/min via a slow speed peristalic pump. An absorbence monitor is placed at the outflow point of the chromatography column and an ultraviolet detector set at 276 nm is used to detect eluting protein fractions. A major protein fraction of about 5 ml elutes from the column under these conditions and is collected in a small beaker. The protein fraction is analyzed using an ACTA III spectophotometer from Beckman Instruments Company. The molarity of the protein fraction is determined to be $2.67 \times 10^{-5}$ wherein the 280 angstrom absorbence coefficient is 0.254, the molecular weight of the protein is 13000 daltons and the extinction coefficient value, E, is 7.3 for a 1% solution.

To the 5 ml of the protein containing eluant collected above is added 1 ml of 1.0 M tris-HCl buffer, pH 8; 1 ml of 1 mM ethylenediaminetetraacetic acid (EDTA); 1 ml of $5 \times 10^{-4}$ M reduced glutathione; 1 ml of $5 \times 10^{-4}$ M of oxidized glutathione and 1 ml of 0.02 M tryptamine-HCl inhibitor. The tryptamine-HCl is added as the inhibitor, while the other reagents (namely, the EDTA and glutathione) are added in accordance with the teaching of Lloyd Chavez, Jr. and Harold Scheraga in "Folding of Ribonuclease, S-Protein and Des (121-124) ribonuclease during Glutathione Oxidation of Reduced Proteins", 1980, *Biochemistry*, 19, 996-1004. The resultant solution shows a pH of 5.5. The solution is stirred for 1.5 hours at the 5.5 pH under slow stirring. Subsequently, the pH is raised to about 8.0 by the addition of 100 mg of tris base crystals. The resulting tris containing solution is stirred slowly at pH 8, at 25° C., for an additional 2.5 hours. A fluffy white precipitate is formed during the stirring process. At the end of the 2.5 hour period, the solution is dialyzed against 1 mM tris-HCl buffer, pH 7.2, containing 0.005 M tryptamine inhibitor. The dialysis membrane is a Spectrapor brand membrane tubing, No. 2 size, having a molecular weight exclusion range of 12-14,000 daltons. The dialysis procedure included two buffer changes with a gross volume of 7000 ml of buffer over a 17 hour period, at 0.5° C., with slow shaking of the dialysis tubing in the dialysis media.

After dialysis, 2 ml of the enzyme-like modified protein containing solution is chromatographed across a Sephadex brand G-15 column, the column dimension being ½ inch × 12 inches, the column being filled with gel filtration agent using 1 mM tris-HCl buffer at pH 7 as the eluant. Such a gel filtration column is used to separate low molecular weight materials from protein materials. The eluant flow rate is 1 ml/min. The eluant was monitored at 254 nm to detect eluting enzyme-like modified protein. A first portion of eluting enzyme-like modified protein is collected and assayed vs. substrate for esterase enzyme. The substrate used is tryptophan methyl ester (TME), the substrate being purchased from Sigma Chemical Company, lot 109C-0048, No. T-5505.

The activity of the esterase enzyme-like modified protein is tested as follows. The protein fraction collected above is assayed by high pressure liquid chromatography (HPLC) to determine activity toward the TME substrate. The assay conditions are as follows. The HPLC column eluant is 0.03 M acetate, pH 6. The column support material is porous silica bonded phase material containing carboxyl side chains. The column is stainless steel composition and is 2 mm × 25 cm, with a flow rate of 4 ml/min. maintained by conventional high pressure pump, for example an Altex, Model 110 A pump. The column eluant is detected by a conventional ultraviolet monitor at 254 nm.

The assay sample is prepared as follows. One ml of the esterase enzyme-like modified protein (with an absorption of 0.222, at 280 nm, equaling 0.335 mg/ml) is admixed with 8 ml of 5 mM tris-HCl buffer, pH 8 and 1 ml of 0.1 M TME substrate. The assay control solution is prepared by adding 8 ml of 5 mM tris-HCl buffer, pH 8, to 1 ml of 0.1 M TME and 1 ml of the tris buffer, pH 7, used as the eluant solution. The pH of both the control and assay sample solution is 6.6.

One ml of the sample is removed from the beaker, using a 2 ml hypodermic syringe, with an 18 gauge needle. The one ml of sample is passed through a 20 microliter injection sample loop onto the HPLC column. The injection time is recorded. This procedure is repeated using the control solution. Both sample and control are chromatographed 4 times in order to obtain a plot of molarity of tryptophan versus time for sample and control to elute from the column.

A statistical analysis is performed with the data obtained from the above procedure which shows a slope of $0.3171 \times 10^{-5}$ M/min, with an error of $0.00685 \times 10^{-5}$ M/min. is determined for the sample. A slope of $0.2878 \times 10^{-5}$ M/min with an error of $0.0091 \times 10^{-5}$ M/min is determined for the control.

The following expression is used to calculate the activity of the esterase enzyme-like modified protein according to the present invention.

$$\text{Activity} = \frac{(\text{change in slope} + \text{error})Vs(10^6)}{MP}$$

wherein: change in slope is the difference between the sample and control slopes (in this example 0.0293); error is the sum of the errors in the sample and control slopes (in this example 0.016); Vs is the sample volume in liters; $10^6$ is micromoles/mole; and MP is mg of modified protein in the assay.

In the above calculation, the concentration of the modified protein is calculated from its absorbance at 280 nm, using the extinction coefficient for ribonuclease, which is 7.3 for a 1% solution. The extinction coefficient is disclosed in the reference entitled *Int. J. Peptide Protein Res.* 5, 49-62 (1973) authored by D. M. Kirschenbaum.

The assay results area as follows:

|  | Substrate<br>TME (Units/g) |
|---|---|
| Initial activity | 0.000 |
| Final activity | 8.0 ± 0.717 |

The results show that the esterase enzyme-like modified protein prepared according to the present invention exhibits activity with respect to the esterase enzyme substrate TME where no activity is previously detected in native ribonuclease enzyme. This illustrates the conversion of one genus of enzyme, namely, a nuclease to a second genus of protein, namely, an esterase enzyme-like modified protein.

The results show that the esterase enzyme-like modified protein prepared according to the present invention exhibits activity with respect to the esterase enzyme substrate TME where no activity is previously detected in native ribonuclease enzyme. This illustrates the conversion of one genus of enzyme, namely, a nuclease, to a second genus of protein, namely, an esterase enzyme-like modified protein.

EXAMPLE 2

One hundred and twenty mg of chromatographically purified bovine pancreatic ribonuclease (RNase) native enzyme, purchased from Sigma Chemical Company, lot 110F- 02051 Type IIA, No. R-5000, is dissolved in 6 ml of 8 M urea containing 0.1 M tris-HCl buffer, pH 8 with slow stirring at 25° C. Next, 0.2 ml of beta-mercaptoethanol denaturing agent is added and the solution is stirred slowly for 15 minutes at 25° C. The solution is then allowed to stand under a nitrogen atmosphere for 16 hours at 25° C. in a stoppered flask. The closed environment is maintained by a pressurized nitrogen tank constantly delivering nitrogen into the flask with the flask vented in to a water trap.

Next, 5 ml of the solution is chromatographed on a Sephadex brand G-15 gel material column which is a 12 inch×1 inch column filled with gel. The column eluant is 0.1 M acetic acid at pH 3. The flow rate of the eluant through the column is 1 ml/min. The absorbence of the outflow of the column is monitored at 276 nm by an ultraviolet detector. A gross protein fraction of 5 ml is collected. The fraction is analyzed on a Beckman Instruments Company ACTA III spectrophotometer. The molarity of the collected protein fraction is determined as $6.64 \times 10^{-5}$ wherein the 280 absorbence is 0.63, the molecular weight of the protein is 13000 daltons and the extinction coefficient value, E, is equal to 7.3 for a 1% solution.

To the 5 ml of protein material collected above is added 0.5 ml of 1.0 M tris-HCl buffer, pH 8; 0.5 ml of 1 mM EDTA; 0.5 ml of $5 \times 10^{-4}$ M reduced glutathione; 0.5 ml of $5 \times 10^{-4}$ M oxidized glutathione and 0.5 ml of 0.02 M tryptamine inhibitor for esterase enzyme. The tryptamine is added as an inhibitor while the EDTA and glutathione are added in accordance with the teaching of Lloyd Chavez, Jr. and Harold Scheraga in "Folding of Ribonuclease, S-Protein and Des (121-124) ribonuclease during Glutathione Oxidation of Reduced Proteins", 1980, *Biochemistry*, 9, 996–1004.

At the end of the 4.0 hour period, resultant solution shows a pH of 5.0. After stirring the resultant solution for 0.5 hours, at the pH 5 value, the pH is raised to 8 with the addition of 100 mg of tris based crystals. The solution is stirred slowly at pH 8 and 25° C. for 4 hours. During the stirring process a fluffy white precipitate forms.

At the end of the 4 hour period, resulting solution is dialyzed against 1 mM tris HCl buffer, at pH 7, containing 2% tryptamine inhibitor. A Spectropor brand membrane dialysis tubing, No. 2 size, with a molecular weight cutoff range of 12-14,000 daltons is used for the dialysis. The dialysis is conducted with two buffer changes for a gross buffer volume of 7000 ml over a 17 hour period, at 0°-5° C. with slow shaking at 0°-5° C.

Two ml of the protein solution above is chromatographed across a Sephadex brand G-15 gel column which is ½ inch×12 inches using as an eluant 1 mM tris-HCl buffer, at pH 7. The eluant flow of rate is 1 ml/min. The absorbence of the eluting solution is monitored at 254 nm. The first half of the eluting protein fraction is collected and assayed against esterase substrate, namely, tryptophan methyl ester (TME) purchased from Sigma Chemical Company, lot 109C-0048, No. T-5505.

The assay for enzymatic activity of the newly synthesized esterase enzyme-like modified protein prepared according to the present invention is performed on a HPLC system. The column is packed with a support material which is a porous silica bonded phase material having carboxyl side chains. The column eluant is 0.03 M acetate at pH 6. The column is of stainless steel composition and 2 mm×25 cm in size. A flow rate of 4 ml/min is maintained by a conventional high pressure pump, for example an Altex, Model 110A pump. The column eluant is detected by a conventional ultraviolet monitor at 254 nm and the tryptophan peak heights are recorded.

The assay sample is prepared as follows. Three ml of the esterase enzyme-like modified protein (with a 280 absorbence of 0.450 at 280 nm, equaling 0.67 mg/ml) is admixed with 6 ml of 1 mM tris-HCl buffer, pH 7.5 and 1 ml of 0.1 M TME substrate. An assay control solution is prepared by adding 6 ml of 1 mM tris-HCl buffer, pH 7.5, to 1 ml of TME substrate and 3 ml of the Sephadex brand G-15 eluant buffer, namely, the 1 mM tris buffer, at pH 7. The pH of both the control and the assay sample is 6.4.

One ml of the sample is removed from the beaker, using a 2 ml. hypodermic syringe, with an 18 gauge needle. The one ml of sample is passed through a 20 microliter injection sample loop onto the HPLC column. The injection time is recorded. This procedure is repeated using the control solution. Both sample and control are chromatographed 4 times in order to obtain a plot of molarity of tryptophan versus time for sample and control to elute from the column.

A statistical analysis is performed with the data obtained from the above procedure which shows a slope of $0.81333 \times 10^{-5}$ M/min., with an error of $0.1021 \times 10^{-5}$ is determined for the sample. A slope of $0.54062 \times 10^{-5}$ M/min with an error of $0.03291 \times 10^{-5}$ M/min is determined for the control.

The following expression is used to calculate the activity of the esterase enzyme-like modified protein according to the present invention.

$$\text{Activity} = \frac{(\text{change in slope} + \text{error}) V_s (10^6)}{MP}$$

wherein: change in slope is the difference between the sample and control slopes (in this example 0.272713); error is the sum of the errors in the sample and control slopes (in this example 0.134); $V_s$ is the sample volume in liters; $10^6$ is micromoles/mole; and MP is mg of modified protein in the assay.

In the above calculation, the concentration of the modified protein is calculated from its absorbance at 280 nm, using the extinction coefficient for ribonuclease, which is 7.3 for a 1% solution. The extinction coefficient is disclosed in the reference entitled *Int. J. Peptide Protein Res.* 5, 49–62 (1973) authored by D. M. Kirschenbaum.

The assay results are as follows:

|  | Substrate TME (Units/g) |
|---|---|
| Initial activity | 0.000 |
| Final activity | 13.62 ± 6.62 |

The results show that the esterase enzyme-like modified protein prepared according to the present invention exhibits activity with respect to the esterase enzyme substrate TME where no activity is previously detected in native ribonuclease enzyme, namely, a nuclease to a second genus of protein, namely, an esterase enzyme-like modified protein.

EXAMPLE 3

One hundred mg of bovine serum albumin (BSA), purchased from Sigma Chemical Company, lot 90F-9315, No. A-7511, is dissolved in 5 ml of 8 M urea containing 0.1 M tris buffer pH 8, with slow stirring at 25° C. Next, 0.2 ml of beta-mercaptoethanol denaturing agent is added to the solution. The solution is shaken slowly for 15 minutes at 25° C. The solution is next placed under a nitrogen atmosphere for 16 hours at 25° C. as disclosed in Example I.

Next, 5 ml of the solution is chromatographed across a gel filtration column, containing Sephadex brand G-15 gel filtration material. The column is 12 inches × 1 inch and is filled with Sephadex brand G-15 gel. Acetic acid at 0.1 M, pH 3, is used as the eluant for the gel column. The eluant flow rate is maintained at 1 ml/min via a slow speed peristalic pump of conventional design. An absorbence monitor is placed at the outflow point of the chromatography column and an ultraviolet detector set at 276 nm is used to detect eluting protein fractions. At the point which protein starts eluting from the column collection is begun and a gross of 5 ml of protein is collected.

To the 5 ml of collected protein is added 1 ml of 1.0 M tris-HCl buffer, pH 8; 1 ml of 1 mM EDTA; 1 ml of $5 \times 10^{-4}$ M reduced glutathione; 1 ml of $5 \times 10^{-4}$ M oxidized glutathione and 1 ml of 0.02 M tryptamine esterase inhibitor. The resultant solution shows a pH of 5.2. The resulting solution is stirred slowly for 0.5 hours at pH 5.2. After 0.5 hours, the pH of the solution is raised to 6 with the dropwise addition of 0.1 M NaOH. The solution at pH 6 is allowed to stir slowly at 25° C. for an additional 4 hours. During the stirring process, a fluffy white precipitate is formed. At the end of the 4 hour period the solution is dialyzed against 1 mM tris-HCl buffer, pH 7, containing 2% tryptamine inhibitor. The tryptophan is added as the inhibitor while other reagents are added as taught by Chavez et al discussed above. The dialysis is performed using a dialysis membrane tubing, namely, Spectrapor brand dialysis tubing, No. 2 size, having a molecular weight exclusion range of 12–14,000 daltons. The dialysis procedure includes 2 buffer changes with a gross buffer volume of 7000 ml of buffer over a 17 hour period, at 0.5° C., with slow shaking of the dialysis tubing in the dialysis media.

After dialysis, 4 ml of the esterase enzyme-like modified protein containing solution is chromatographed across a Sephadex brand G-10 column, the column dimension being ½ inch × 12 inches and filled with gel agent using 1 mM tris-HCl buffer at pH 7 as the eluant. The eluant outflowing from flow rate is 1 ml/min. The eluant of the column is monitored at 254 nm to detect eluting enzyme-like modified protein. A first portion of eluting enzyme-like modified protein is collected and assayed against substrate for esterase enzyme. The substrate used is tryptophan methyl ester (TME), the substrate being purchased from Sigma Chemical Company, lot 109C-0048, No. T-5505.

The activity of the esterase enzyme-like modified protein is tested as follows. The protein fraction collected above is assayed by HPLC to determine activity toward the TME esterase substrate. The assay conditions are as follows. The HPLC column eluant is 0.03 M acetate, pH 6. The column support material is a porous silica bonded phase material containing carboxyl side chains. The column is stainless steel composition and is 2 mm × 25 cm, with an eluant flow rate of 4 ml/min. maintained by a conventional high pressure pump, for example an Altex, Model 110A pump. The column eluant is detected by a conventional ultraviolet monitor at 254 nm and at 0.05 A.

The assay sample is prepared as follows. Five ml of 0.03 M acetate buffer, pH 6, is mixed with 1 ml of 0.1 mM TME and with 4 ml of the esterase enzyme like modified protein prepared above (with an adsorption at 280 nm of 0.016 equaling 0.024 mg/ml). The assay control is prepared by adding 5 ml of 0.03 M acetate pH 6 to 1 ml of 0.1 M TME and to 4 ml of the eluant, namely, the tris-HCl buffer, pH 7. Both the control solution and the assay sample solution show pH 5.8.

One ml of the sample is removed from the beaker, using a 2 ml hypodermic syringe, with an 18 gauge needle. The one ml of sample is passed through a 20 microliter injection sample loop onto the HPLC column. The injection time is recorded. This procedure is repeated using the control solution. Both sample and control are chromatographed 4 times in order to obtain a plot of molarity of tryptophan versus time for sample and control to elute from the column.

A statistical analysis is performed with the data obtained from the above procedure which shows a slope of $0.05596 \times 10^{-5}$ M/min., with an error of $0.00213 \times 10^{-5}$ M/min is determined for the sample. A slope of $0.6244857 \times 10^{-5}$ M/min. with an error of $0.000823 \times 10^{-5}$ M/min is determined for the control.

The following expression is used to calculate the activity of the esterase enzyme-like modified protein according to the present invention.

$$\text{Activity} = \frac{(\text{change in slope} + \text{error}) \text{Vs}(10^6)}{MP}$$

wherein: Change in slope is the difference between the sample and control slopes (in this example 0.0314); error is the sum of the errors in the sample and control slopes (in this example 0.00296); Vs is the sample volume in liters; $10^6$ is micromoles/mole; and MP is mg of modified protein in the assay.

In the above calculation, the concentration of the modified protein is calculated from its absorbance at 280 nm, using the extinction coefficient for ribonuclease, which is 6.62 for a 1% solution. The extinction coefficient is disclosed in the reference entitled *Int. J. Peptide Protein Res.* 5, 49–62 (1973) authored by D. M. Kirschenbaum.

The assay results are as follows:

|  | Substrate<br>TME (Units/g) |
|---|---|
| Initial Activity | 0.00 |
| Final Activity | 32.7 ± 3.08 |

The results show that the esterase enzyme-like modified protein prepared according to the present invention exhibits activity with respect to the esterase enzyme substrate TME.

No esterase activity is previously detected in the native BSA protein.

This illustrates the conversion of one genus of nonenzymatic protein, an albumin, to another genus of protein, an enzymatically active esterase enzyme-like modified protein.

EXAMPLE 4

Two hundred fifty mg of BSA, purchased from Sigma Chemical Company, lot 90F-8351, No. 7511, is dissolved in 25 ml of 8 M urea with slow stirring, at pH 7.8 for 2 hours at 25° C. After the 2 hour stirring period, 1 ml of 10 mM beta-mercaptoethanol reducing agent solution is added. The resulting solution is stirred slowly for 1 hour, at pH 7.6, at 25° C.

Next, 75 ml of a 1% solution of tryptamine esterase enzyme inhibitor is added. The solution is slowly stirred for 2 hours, at pH 7.0.

Next, the protein is cross-linked as follows. The solution containing the protein is placed in a dialysis bag which is Spectrapor brand dialysis tubing, No. 2 type. The protein contained in the dialysis bag is dialyzed against 1% tryptamine inhibitor solution in 1 mM tris buffer at pH 7.0, at 0°–5° C. for 17 hours.

The resultant esterase enzyme-like modified protein is purified as follows. Two ml of the preparation above is chromatographed across a Sephadex G-10 chromatography column using 0.03 M acetate buffer pH 6, as the eluant. The eluant flow rate is 2 ml/min. The initial half of the protein peak is approximately 5 ml of eluant volume and exhibits an absorbance of 0.666 at 280 nm.

The activity of the esterase enzyme-like modified protein prepared above is tested as follows. The protein fraction collected above is assayed by HPLC. The column support material is porous silica bonded phase material containing carboxyl side chains. The column is stainless steel composition and is 2 mm×25 cm. The eluant flow rate is 4 ml/min. using 0.03 M acetate, pH 6.

The column eluant protein fraction is detected by a conventional ultraviolet monitor at 254 nm.

The assay sample is prepared as follows. Five ml of 0.03 M acetate, pH 6, is admixed with 1 ml of 0.1 M TME and 4 ml of the protein containing solution above. The assay control solution is prepared by admixing 9 ml of 0.03 M acetate, pH 6, with 1 ml of 0.1 M TME substrate. The pH of both the control and assay sample solution is 6.0.

One ml of the sample is removed from the beaker, using a 2 ml hypodermic syringe, with an 18 gauge needle. The 1 ml of sample is injected through a 20 microliter injection sample loop onto the HPLC column. The injection time is recorded. This procedure is repeated using control solution. Both sample and control are chromatographed 4 times in order to obtain a plot of molarity of tryptophan versus time for sample and control to elute from the column.

A statistical analysis is performed with the data obtained from the above procedure which shows a slope of $0.0516 \times 10^{-5}$ M/min., with an error of 0.004 M/min for the sample. A slope of $0.0287 \times 10^{-5}$ M/min with an error of $0.0016 \times 10^{-5}$ M/min for the control.

The following expression is used to calculate the activity of the esterase enzyme-like modified protein according to the present invention.

$$\text{Activity} = \frac{(\text{change in slope} + \text{error}) \text{Vs}(10^6)}{MP}$$

wherein:
change in slope is the difference between the sample and control slopes;
error is the sum of the errors in the sample and the control slope;
Vs is the sample volume in liters;
$10^{+6}$ is micromoles/mole; and
MP is mg of modified protein in the assay.

In the above calculation, the concentration of the modified protein is calculated from its absorbence at 280 nm, using the extinction coefficient for bovine serum albumen, which is 6.6280 for a 1% solution. The above procedure is disclosed in the reference entitled *Int J.Peptide Protein Res.* 5, 49–62 (1973) authored by D. M. Kirschenbaum.

The assay results are as follows.

|  | Substrate<br>TME (Units/g) |
|---|---|
| Initial Activity | 0.0 |
| Final Activity | 0.57 ± .16 |

The results show that the modified esterase enzyme-like protein prepared according to the present invention exhibits activity with respect to esterase enzyme substrate TME. No activity with respect to esterase substrate TME is previously detected in the native BSA.

This illustrates the conversion of one genus of nonenzymatic protein, an albumin to another genus of protein, namely, an enzymatically active esterase enzyme-like modified protein.

EXAMPLE 5

To demonstrate that native bovine serum albumin (BSA) protein shows no catalytic activity with respect to the L-tryptophan methyl ester (TME) substrate of Example 4 above, the following control procedure is performed.

One g of BSA, from Sigma Chemical Company, Type 7511, lot 90F-9315, is dissolved in 25 ml of distilled deionized water, with slow stirring at 25° C. To this solution is added 75 ml of a 1% tryptamine-HCl solution. The resulting solution is incubated for 15 minutes at 25° C. This solution is next dialyzed in a No. 2 sized Spectra/Por ® dialysis tube against 3500 ml of a 1% tryptamine-HCl solution for four hours. The No. 2 tubing has a molecular weight exclusion range of 12-14,000 daltons. The temperature of the solution is maintained at 0°-5° C. and the pH at 6.0 during the dialysis procedure. After the four hour dialysis procedure, two ml of the solution is chromatographed across a Sephadex brand G-10 gel chromatography column. The column is eluted with 0.03 M acetate buffer, pH 6, at a flow rate of 2 ml/min. The column size is 25 inch × ½ inch.

Two distinct peaks are collected. The first peak is eluted about 30 ml. The first peak is identified by a 300-200 nm scan on an ACTA 3 Spectrophotometer (Beckman Instruments Company) as being BSA protein. The second peak is eluted at 60 ml and is identified by ultraviolet spectrophotometry as tryptamine.

Four ml of the collected BSA is next assayed versus TME substrate for possible enzymatic activity. The assay is conducted as follows. A high pressure liquid chromatography system is used for the assay. The column is a 2 mm × 25 cm, stainless steel column packed with porous silica particles containing carboxyl size chains, with an average particle pore size of 40 microns, purchased from Baker Chemical Company.

The column eluant is 0.03 M acetate, pH 6, at a flow rate of 4 ml/min. The absorbance of the outflow of the column is monitored at 254 nm. Five ml of the 0.03 M acetate, pH 6 and 1 ml of 0.1 M TME substrate are mixed with 4 ml of the BSA solution above.

The assay control is prepared by mixing 9 ml of 0.03 M acetate, pH 6 and 1 ml of 0.1 M TME substrate. The pH of both the control and sample is 6.0.

One ml of the assay sample is removed from a sample beaker with a 2 ml hypodermic syringe with an 18 gauge needle and injected through a 20 microliter injection sample loop onto the column. The time of injection is recorded.

The procedure is then repeated using the assay control solution. Both the sample solution and control solution are chromatographed four times in order to obtain a plot of molarity of TME versus time for the assay sample and the assay control solutions.

A statistical analysis of the data obtained shows a slope of $0.19689 \times 10^{-5}$ M/min, with an error of $0.0089 \times 10^{-5}$ M/min for the BSA assay sample. For the assay control sample, a slope of $0.20296 \times 10^{-5}$ M/min, with an error of $0.0062 \times 10^{-5}$ M/min is determined. The slopes, plus the sums of the errors, are virtually identical. Accordingly, the native BSA protein shows no measurable catalytic activity properties with respect to TME substrates.

EXAMPLE 6

To demonstrate that native ribonuclease enzyme shows no catalytic activity with respect to L-tryptophan methyl ester (TME) substrate of Examples 1-2 above, the following control is performed.

Sixty mg of ribonuclease enzyme, from Sigma Chemical Company, Type R-5000, lot 20F-2010, is dissolved in 100 ml of 1 mM tris buffer, at pH 7, with slow stirring at 25° C.

The ribonuclease containing solution is then dialyzed using a No. 3 Spectra/Por ® dialysis tube against 3500 ml of 1 mM tris buffer, pH 7, for 17 hours at 0°-5°. The No. 3 tubing has a molecular weight exclusion range of 35-4500 daltons. Next, 1 ml of the ribonuclease containing solution is assayed versus TME substrate for possible enzymatic activity with respect to TME. The assay is conducted as follows.

A high pressure liquid chromatography system is used for the assay. The column is a 2 mm × 25 cm stainless steel column packed with porous silica containing carboxyl side chains having an average pore size of 40 microns, purchased from Baker Chemical Company. The column eluant is 0.03 M acetate, pH 6, at a flow rate of 7 ml/min. The absorbance of the column outflow is monitored at 280 nm.

The assay sample solution containing native ribonuclease is prepared as follows. Eight ml of one mM tris buffer, pH 8.05, is admixed with one ml of 0.1 M TME, pH 3.4 and 1 ml of the ribonuclease solution prepared above. The assay control solution is prepared by admixing 8 ml of 1 mM tris buffer, pH 8.05; one ml of 0.1 M TME, pH 3.4 and one ml of one mM tris buffer, pH 7.0. The pH of the control and assay solutions is 6.5.

Next, one ml of the assay sample solution is removed from the sample beaker using a 2 ml hypodermic syringe with an 18 gauge needle and injected onto the column through a 20 microliter injection sample loop. The time of injection is recorded.

This procedure is then repeated using the assay control solution. Both sample and control solutions are chromatographed four times in order to obtain a plot of molarity of TME versus time for sample and control solutions.

A statistical analysis of the data obtained shows virtually identical slopes of $0.1400 \pm 0.003$ for both control and sample solutions. Accordingly, the native ribonuclease shows no measurable catalytic activity properties with respect to the TME substrate.

EXAMPLE 7

To demonstrate that native bovine serum albumin (BSA) activity with respect to L-tryptophan methyl ester (TME) substrate of Example 3 above, the following control is performed.

One hundred mg of BSA from Sigma Chemical Company, No. 7511, lot 90F-8351, is dissolved in 100 ml of one mM tris buffer at pH 7, with slow stirring at 25° C.

The BSA containing solution is then dialyzed using a No. 2 Spectra/Por ® dialysis tube against 3500 ml of 1 mM tris buffer, pH 7, for 17 hours at 0°-5° C. The No. 2 tubing has a molecular weight exclusion range of 12–14,000 daltons. Next, one ml of the BSA containing solution is assayed versus TME substrate for possible enzymatic activity with respect to TME. The assay is conducted as follows.

A high pressure liquid chromatography system is used for the assay. The column is a 2 mm×25 cm stainless steel column packed with porous silica containing carboxyl side chains having an average pore size of 40 microns, purchased from Baker Chemical Company. The column eluant is 0.03 M acetate, pH 6, at a flow rate of 7 ml/min. The absorbance of the column outflow is monitored at 280 nm.

The assay sample solution containing native BSA is prepared as follows. Eight ml of one mM tris buffer, pH 7.5 is admixed with one ml of 0.1 M TME, pH 3.2 and one ml of the ribonuclease solution prepared above. The assay control solution is prepared by admixing 8 ml of one mM tris buffer, pH 7.5, one ml of 0.1 M TME, pH 3.2 and one ml of one mM tris buffer, pH 7.0. The pH of the control and assay solutions is 5.8.

Next, one ml of the assay sample solution is removed from the sample beaker using a 2 ml hypodermic syringe with an 18 gauge needle and injected onto the column through a 20 microliter injection sample loop. The time of injection is recorded.

This procedure is then repeated using the assay control solution. Both sample and control solutions are chromatographed four times in order to obtain a plot of molarity of TME versus time for sample and control solutions.

A statistical analysis of the data obtained shows virtually identical slopes of 0.06±0.0065 for both control and sample solutions. Accordingly, the native ribonuclease shows no measurable catalytic activity properties with respect to the TME substrate.

What is claimed is:

1. A process for chemically altering the substrate specificity of a native protein to produce an enzyme-like modified protein, comprising:
   a. selecting an enzyme to be modeled;
   b. grossly denaturing a native protein;
   c. partially renaturing said grossly denatured native protein to produce a partially denatured protein;
   d. contacting said partially denatured protein with an inhibitor for said model enzyme to form a partially denatured protein-model enzyme inhibitor complex; and
   e. cross-linking said partially denatured protein in said protein-inhibitor complex.

2. The process of claim 1 wherein said native protein is grossly denatured by forming an aqueous solution of said native protein and maintaining said aqueous solution at a temperature and for a time sufficient to grossly denature said native protein.

3. The process of claim 2 wherein said temperature is between 50 and 70 degrees centigrade.

4. The process of claim 1 wherein said native protein is grossly denatured by admixing said native protein with water to form an aqueous solution and admixing the resulting aqueous solution with a denaturing agent.

5. The process of claim 4 wherein said denaturing agent is an organic acid.

6. The process of claim 5 wherein said organic acid is selected from the group consisting of acetic acid, formic acid, propionic acid and citric acid.

7. The process of claim 4 wherein said denaturing agent is an inorganic acid.

8. The process of claim 7 wherein said inorganic acid is selected from the group consisting of nitric acid, phosphoric acid, sulfuric acid and hydrochloric acid.

9. The process of claim 4 wherein said denaturing agent is guanidine hydrochloride.

10. The process of claim 4 wherein said denaturing agent is urea.

11. The process of claim 4 wherein said denaturing agent is a mixture of urea and beta-mercaptoethanol.

12. The process of claim 1 wherein said partially denatured protein is cross-linked by contacting said protein with a crosslinking agent.

13. The process of claim 12 wherein said cross-linking agent is glutaraldehyde.

14. A process for chemically altering the substrate specificity of a native protein to produce an enzyme-like modified protein, comprising:
   a. selecting an enzyme to be modeled;
   b. grossly denaturing a native protein;
   c. admixing said grossly denatured protein with an inhibitor of said model enzyme;
   d. partially renaturing said grossly denatured protein, in the presence of said inhibitor, to produce a partially denatured protein inhibitor-complex; and
   e. cross-linking said partially denatured protein portion of said protein-inhibitor complex.

15. The process of claim 14 wherein said native protein is grossly denatured by forming an aqueous solution of said native protein and maintaining said aqueous solution at a temperature and for a time sufficient to grossly denature said native protein.

16. The process of claim 15 wherein said temperature is between 50° and 70° C.

17. The process of claim 14 wherein said native protein is grossly denatured by admixing said native protein with water to form an aqueous solution and admixing the resulting aqueous solution with a denaturing agent.

18. The process of claim 17 wherein said denaturing agent is an organic acid.

19. The process of claim 18 wherein said organic acid is selected from the group consisting of acetic acid, formic acid, propionic acid and citric acid.

20. The process of claim 17 wherein said denaturing agent is an inorganic acid.

21. The process of claim 20 wherein said inorganic acid is selected from the group consisting of nitric acid, phosphoric acid, sulfuric acid and hydrochloric acid.

22. The process of claim 17 wherein said denaturing agent is guanidine hydrochloride.

23. The process of claim 17 wherein said denaturing agent is urea.

24. The process of claim 17 wherein said denaturing agent is a mixture of urea and beta-mercaptoethanol.

25. The process of claim 14 wherein said partially denatured protein is cross-linked by contacting said protein with a cross-linking agent.

26. The process of claim 25 wherein said cross-linking agent is glutaraldehyde.

27. The enzyme-like modified protein product of the process of claim 1.

28. The enzyme-like modified protein product of the process of claim 14.

* * * * *